United States Patent [19]

Keel et al.

[11] Patent Number: 4,474,985

[45] Date of Patent: Oct. 2, 1984

[54] PURIFICATION OF N-ACETYL AMINOPHENOLS

[75] Inventors: Billy L. Keel, Arnold; Irvin S. Klaus, St. Louis; Marvin L. Oftedahl, Warson Woods, all of Mo.

[73] Assignee: Monsanto Company, St. Louis, Mo.

[21] Appl. No.: 462,495

[22] Filed: Jan. 31, 1983

Related U.S. Application Data

[63] Continuation-in-part of Ser. No. 280,045, Jul. 6, 1981, abandoned, which is a continuation of Ser. No. 130,809, Mar. 17, 1980, abandoned.

[51] Int. Cl.³ .................................... C07C 103/38
[52] U.S. Cl. .................................... 564/216; 252/402; 564/4
[58] Field of Search .................. 564/4, 216; 252/402

[56] References Cited

U.S. PATENT DOCUMENTS

| | | | |
|---|---|---|---|
| 2,625,557 | 1/1953 | Cottle et al. | 260/562 A X |
| 2,654,722 | 10/1953 | Young et al. | 260/562 A X |
| 2,799,692 | 7/1957 | Croxall et al. | 260/562 A X |
| 2,822,370 | 2/1958 | Cottle et al. | 260/562 A X |
| 2,945,870 | 7/1960 | Young | 260/562 A X |
| 2,998,450 | 8/1961 | Wilbert et al. | 260/562 A |
| 3,042,719 | 7/1962 | Hahn et al. | 260/562 A |
| 3,081,321 | 3/1963 | Young | 260/562 A X |
| 3,081,322 | 3/1963 | Young | 260/562 A X |
| 3,113,150 | 12/1963 | Young | 260/562 A |
| 3,458,574 | 7/1969 | Anselm et al. | 260/562 A |
| 3,748,358 | 7/1973 | Baron | 260/562 A |
| 3,781,354 | 12/1973 | Kosak | 260/562 B |
| 3,917,695 | 11/1975 | Schulman et al. | 260/562 A |

*Primary Examiner*—Thomas A. Waltz
*Attorney, Agent, or Firm*—Jon H. Beusen; James C. Logomasini; Arnold H. Cole

[57] ABSTRACT

A process for increasing the color-free shelf life of a crude N-acetyl aminophenol prepared by the acetylation of an aminophenol wherein the N-acetyl aminophenol contains color-forming impurities which are the products of oxidation of the aminophenol and other side reactions. The process comprises dissolving the crude N-acetyl aminophenol in a solvent containing a reducing agent, heating the solution at about the boiling point, crystallizing the N-acetyl aminophenol from the solution, washing the crystalline N-acetyl aminophenol with solvent containing reducing agent and thereafter separating and drying the crystalline N-acetyl aminophenol.

3 Claims, No Drawings

PURIFICATION OF N-ACETYL AMINOPHENOLS

CROSS REFERENCE TO RELATED APPLICATIONS

This is a continuation-in-part of copending application Ser. No. 280,045, filed July 6, 1981. Now abandoned which was a continuation of application Ser. No. 130,809, filed March 17, 1980, now abandoned.

BACKGROUND OF THE INVENTION

1. Field Of The Invention

This invention relates to a process for decolorizing the colored impurities which occur during the preparation of an N-acetyl aminophenol.

In the past, acylated aminophenols have been used as non-volatile antioxidants for petroleum products, greases, synthetic lubricants and the like. Of this class of acetylated aminophenols, the lower molecular weight members, particularly the N-acetyl alkyl-substituted aminophenols containing lower alkyl nuclear substituents, i.e., having from 1 to 4 carbon atoms, and especially N-acetyl-p-aminophenol, have found extensive use in the pharmaceutical industry as analgesics.

It is well known that aminophenols, and especially ortho- and para-aminophenols, oxidize readily to afford quinone, quinonimine and meriquinonimine color body impurities which impart discoloration to the aminophenol. These impurities are present in crude N-acetyl aminophenol products prepared by reacting aminophenol with an acetylating agent such as acetic anhydride, mixtures of acetic anhydride in acetic acid, acetic acid and the like. When the crude N-acetyl aminophenol is to be used for medicinal purposes or as intermediates in the preparation of other compounds having medicinal use, the N-acetyl aminophenol must be treated so that it is essentially color-free and retains that state over prolonged periods of storage.

2. Prior Art

N-acetyl aminophenols have customarily been prepared by acetylation of an aminophenol, such as p-aminophenol, with acetic acid or acetic anhydride at atmospheric pressure and temperatures ranging from room temperature to 130° C. There are may variations of this general procedure known to those skilled in the art. An unsatisfactory product is generally obtained due to the readily oxidizable nature of aminophenols and the consequent formation of colored impurities which are carried over to the acetylated product.

Various methods for the decolorization and purification of aminophenols and N-acetyl aminophenols have been suggested.

For example, U.S. Pat. No. 2,013,394 purifies the aminophenol by filtration, alkaline precipitation in the presence of sodium sulfite and solvent extraction. U.S. Pat. No. 2,478,114 treats the aminophenol with reducing agents such as sulfides and sulfites. U.S. Pat. No. 3,917,695 purifies p-aminophenols with acid and aromatic amines or by solvent extraction. U.S. Pat. No. 2,822,370 treats acyl aminophenol with a hot aqueous alkaline steam distillation and subsequent filtration. U.S. Pat. No. 2,945,870 uses a boron condensation catalyst during the initial acetylation reaction and subsequently filters the product with characoal. U.S. Pat. No. 3,042,719 purifies N-acetyl aminophenols by dissolving the N-acetyl aminophenol in water, acidifying the water solution, and filtering with the addition of an alkaline reducing sulfite, e.g., ammonium and alkali metal sulfites, bisulfites and hydrosulfites, U.S. Pat. Nos. 3,081,321 and 3,081,322 acetylated p-aminophenol in the presence of a boron-containing catalyst followed by charcoal filtration. U.S. Pat. No. 3,113,150 filters N-acetyl-p-amino-phenol with carbon black. U.S. Pat. No. 3,748,358 filters N-acetyl-p-aminophenol with the acid treated carbon and a metal chelating agent. U.S. Pat. No. 3,781,354 contacts N-acetyl-p-aminophenol at elevated temperatures with ferric chloride and activated carbon.

Although the various methods described above are all effective to a certain degree in obtaining an N-acetyl aminophenol which is relatively color-free, the decolorized N-acetyl aminophenol may tend to regain its coloration over time due to oxidation. Thus, formulation of an N-acetyl aminophenol into a pharmaceutical product and subsequent warehouse and retail storage of the pharmaceutical product, e.g., analgesic tablets, will result in a product which gradually degrades in color from the original white product.

SUMMARY OF THE INVENTION

This invention is directed to a process for increasing the color-free shelf life of an N-acetyl aminophenol which has been prepared from the corresponding aminophenol, said N-acetyl aminophenol containing, as color-producing impurities, the products of oxidation of the aminophenol. The process of the invention comprises the formation of a solution of the crude N-acetyl aminophenol resulting from the initial condensation reaction of the aminophenol with acetic acid or acetic anhydride. The solution contains formamidine-sulfinic acid ("FS") and sodium metabisulfite ("SMB"). The solution containing the FS and SMB is then heated at about the boiling point and held for a short period. The solution is then subjected to crystallizing conditions to separate the N-acetyl aminophenol from the solution. The crystallized N-acetyl aminophenol is then washed with additional solvent preferably containing a reducing agent, such as SMB, and is then filtered or centrifuged to remove it from solution and subsequently dried to afford an N-acetyl aminophenol having increased color-free shelf life.

DESCRIPTION OF THE INVENTION

As set forth above, the process of this invention is directed to increasing the color-free shelf life of an N-acetyl aminophenol. The material which is subjected to the process of this invention is the so-called crude N-acetyl aminophenol which is the direct reaction product of the acetylation of an aminophenol with acetic acid, acetic anhydride or mixtures thereof in a suitable reaction vessel and under conditions well known to those skilled in the art as set forth in the patents described in the section set forth above entitled "Prior Art".

In general, the process comprises forming a solution of a crude N-acetyl aminophenol and a solvent therefor which contains FS and SMB. The solution is then heated at about the boiling point thereof and the N-acetyl aminophenol is subsequently crystallized from solution. The crystalline N-acetyl aminophenol is then washed with additional solvent preferably containing a reducing agent, such as SMB, and separated from the solution and dried. The dried, crystalline N-acetyl aminophenol thus produced exhibits increased color-free shelf life as compared to N-acetyl aminophenol which has not been so treated.

The N-acetyl aminophenols which can be treated in accordance with the present invention include N-acetyl aminophenol as well as N-acetyl amino carbacrol, N-acetyl amino thymol, N-acetyl 2,5-dimethyl-4-aminophenol, N-acetyl 2-methyl-4-aminophenol, N-acetyl 3-methyl-4-aminophenol, N-acetyl 2,5-diethyl-4-aminophenol, N-acetyl 3-butyl-4-aminophenol and other N-acetyl alkyl-substituted aminophenols containing lower alkyl nuclear substituents, i.e., having from 1 to 4 carbon atoms. The process of this invention is particularly useful for treating N-acetyl aminophenols, as described above, in which the amino group is in a position ortho or para to the hydroxy group (i.e., other than meta with respect to each other).

The solvent which is used to form the initial solution of crude N-acetyl aminophenol may be any inert solvent which will dissolve the N-acetyl aminophenol and which will also act as a solvent for the FS and and SMB which are added thereto and which may be heated to a sufficiently high temperature to afford the greatest efficiency of FS as a reducing agent. Suitable solvents include mixtures of alcohols and water such as isopropanol/water, methanol/water, ethanol/water as well as water alone.

The solution of N-acetyl aminophenol in solvent is prepared so that the solution contains about 30 percent solids/70 percent solvent when the solvent is about 70 percent water, e.g., 30 percent by volume isopropanol in water.

To the solution there is added from about 0.05 to about 10 parts FS, preferably from about 0.2 to about 1.0 part, and from about 0.05 to about 10 parts SMB, preferably from about 0.2 to about 1.0 part. Especially preferred is from about 0.4 to about 0.6 part each of FS and SMB.

The solution thus formed is heated to a temperature of from about 70° to about 100° C., preferably from about 75° to about 90° C. A temperature of about 85° C. is especially preferred when using aqueous isopropanol.

It is critical to the present process that the temperature of the solution be at about the boiling point of the solution and that the temperature be held at that level for a short period, i.e., at least for about 5 to about 60 minutes. Preferably the solution is held at that temperature for about 10 to 20 or 30 minutes.

The temperature is then lowered to a temperature of from about 70° to about 50° C., depending on the particular solvent, in order to crystallize the N-acetyl aminophenol from the solution.

The crystalline N-acetyl aminophenol is then washed with additional solvent, preferably containing a reducing agent such, as SMB, from about 0.05 to about 1.0 part, preferably from about 0.1 to about 0.3 part.

The N-acetyl aminophenol is then separated from the solution by filtration or centrifugation and then dried by heating by any conventional means known to those skilled in the art in order to afford the crystalline N-acetyl aminophenol.

In the following Examples, N-acetyl-p-aminophenol will be used for illustrative purposes, but it should be understood that the process of this invention is considered to have equal applicability to N-acetyl aminophenols other than N-acetyl-p-aminophenol and which are more specifically set forth above. In these Examples, parts are given as parts by weight based on N-acetyl-p-aminophenol.

EXAMPLE I

Crude N-acetyl-p-aminophenol (100 parts) is dissolved in 233 parts aqueous isopropanol (25 percent by weight isopropanol) containing formamidinesulfinic acid (0.4 part) and sodium metabisulfite (0.3 part) by heating. The solution is held at 85°–89° C. for 15–20 minutes, then cooled to 10° C. The resulting crystalline N-acetyl-p-aminophenol is filtered, washed and dried. The material meets U.S.P. color specifications and its color is suitable for pharmaceutical formulations.

Repeating the above Example in the absence of formamidinesulfinic acid and sodium metabisulfite results in a crystalline N-acetyl-p-aminophenol which is too highly colored for use in pharmaceutical formulations.

EXAMPLE II

The procedure of Example I was repeated. Sampling each run at the point of filtration and at the point of packaging showed that the material prepared in the absence of FS and SMB degraded rapidly in color and that the color increased nearly two-fold in the short time between the sampling at the filtration point and the packaging point.

In contrast, the material prepared using FS and SMB did not degrade in color between the filtration and packaging points and, after nearly a year, the material continued to indicate color stability.

EXAMPLE III

About 100 g of N-acetyl-p-aminophenol was dissolved, with stirring under a nitrogen atmosphere, in about 400 g of water, along with the stabilizer being evaluated. Four runs were done. Run 1 had no stabilizer; Run 2 had about 0.6% SMB; Run 3 had about 0.6% FS; and Run 4 had about 0.3% SMB and about 0.3% FS. The solutions were each heated to about 95° C. and held above 85° C. for about 20 minutes. The solutions were each cooled to about 20° C. Crystalline N-acetyl-p-aminophenol was recovered and washed with about 50 ml of cold water containing about 0.1% SMB. After drying, the crystalline N-acetyl-p-aminophenol was subjected to two color tests, measuring limit of color and pinking tendency.

The first test, limit of color, measures colored impurities produced during synthesis of the N-acetyl-p-aminophenol. The test is accomplished by making a slurry of about 20 g of N-acetyl-p-aminophenol in about 20 ml of ethanol, decanting and centrifuging the supernatant liquid, and measuring the absorbance of the supernatant liquid at 420 nm. The limit of color of Run 1, with no stabilizers, was 0.059; Run 2, with about 0.6% SMB, was 0.026; Run 3, with about 0.6% FS was 0.036; and Run 4, with about 0.3% SMB, was 0.035.

This invention is somewhat effective in lowering the limit of color. However, this invention is much more effective in reducing pinking which results from formation of color bodies during storage and is believed to be caused by oxidation upon standing.

In the second test, measuring pinking tendency, N-acetyl-p-aminophenol was dissolved in water at about 95°–100° C., and the solution was allowed to cool slowly to room temperature. This solution was observed over 24 hours for appearance of any pink color. In this Example, Run 1 with no stabilizer developed the strongest pink color. Run 2, with 0.6% SMB, and Run 3, with 0.6% FS each developed some pink color. And, Run 4 with 0.3% SMB and 0.3% FS developed only a very slight pink color.

The limit of color and pinking tendency are unrelated phenomena. The usefulness of this invention is primarily in reducing pinking and secondarily in reducing limit of color.

What is claimed is:

1. A process for increasing the color-free shelf life of an N-acetyl aminophenol, prepared from the corresponding aminophenol, said N-acetyl aminophenol containing, as color-forming impurities, the products of oxidation of said aminophenol and other impurities, said process comprising (a) forming a solution of crude N-acetyl aminophenol in a solvent therefor containing formamidinesulfinic acid and sodium metabisulfite, (b) heating said solution at about the boiling point thereof, (c) cooling said solution to crystallize the N-acetyl aminophenol from said solution, (d) washing the crystalline N-acetyl aminophenol with additional solvent containing sodium metabisulfite, and (e) separating and drying the crystalline N-acetyl aminophenol.

2. The process of claim 1 wherein said solvent is isopropanol/water.

3. The process of claim 1 wherein said solvent is water.

* * * * *